United States Patent [19]

Goldstein

[11] Patent Number: 5,503,615
[45] Date of Patent: Apr. 2, 1996

[54] IMPLANTABLE CARDIAC VENTRICULAR ASSIST DEVICE AND CONTROLLER THEREOF

[76] Inventor: Bernard Goldstein, 24311 Majestic Blvd., Oak Park, Mich. 48237

[21] Appl. No.: 296,479

[22] Filed: Aug. 26, 1994

[51] Int. Cl.⁶ .................................................. A61M 1/10
[52] U.S. Cl. ................................................ 600/16; 600/17
[58] Field of Search ........................... 600/16, 17; 623/3; 415/900

[56] References Cited

U.S. PATENT DOCUMENTS

| | | | |
|---|---|---|---|
| 4,643,641 | 2/1987 | Clausen et al. | 415/900 |
| 5,055,005 | 10/1991 | Kletschka | 600/75 |

OTHER PUBLICATIONS

Tanaka et al, "Transactions Of The ASME", vol. 109, Aug. 1987, pp. 272–278.

*Primary Examiner*—William E. Kamm

[57] ABSTRACT

An implantable ventricular assist device is described which has only one moving part. This part consists of a conical rotor with vanes which spiral upward from the base in a direction opposite to the direction of rotation. There are no valves within the device itself, but one or two valves are situated in the conduits connected to it. The device is powered by a constant running electric motor which screws into the base of the rotor housing. The motor is connected to a portable external battery by means of subcutaneous electrical leads.

8 Claims, 4 Drawing Sheets

BOTTOM VIEW

IMPLANTABLE CARDIAC VENTRICULAR ASSIST DEVICE AND CONTROLLER THEREOF

FIELD OF THE INVENTION

The invention described herein is a device designed to supplant or replace the pumping functions of a human or animal heart in instances where the heart cannot provide satisfactory perfusion. The pump is capable of delivering physiological blood pressures with minimal damage to the cellular components of the fluid.

BACKGROUND OF THE INVENTION

Following a severe cardiac episode pumping volumes drop upwards of 50%. With such poor perfusion vital organs such as the brain, liver and kidneys are quickly damaged. Often heart transplant is not a viable solution due to the immune response to the foreign tissue as well as the limited availability of donor organs. Efforts to produce even temporary artificial hearts have largely been unsuccessful.

A deficiency common to artificial heart devices has been excessive thrombosis and embolization. These life threatening occurrences result from crushing or shearing blood elements by mechanical means. The use of rigid construction materials for vanes, screws and valves is principally responsible for these problems.

The use of differential pressures on a plenum to force blood from a cavity in itself lessens the cell damage; however, the need for ball or flap valves to prevent back flow merely shifts the location of cellular damage. Appreciable stagnation within the bladder also characterizes this design, thereby facilitating thrombosis. In addition, the need for an external compressor diminishes the quality of life and leaves the recipient vulnerable to infection via the tubes exiting the chest cavity. Plenum type designs have been utilized previously and are exemplified by U.S. Pat. Nos. 4,058,857 (Runge et al 1977), 4,994,078 (Jarvik 1991), and 5,286,849 (Kolffet al 1994), which are incorporated herein by reference.

High speed rotary and helical pumps have often suffer reliability problems and exacerbate the problems of aforementioned corpuscular damage. High speed rotary and helical pumps have been developed extensively; U.S. Pat. Nos. 4,704,121 (Moise 1987), 4,927,407 (Dorman 1990) and 4,995,857 (Arnold 1991) are examples of these types of design and are incorporated herein by reference.

Another approach to subsidizing cardiac output has involved centrifugal pumps. A centrifugal pump is defined to include radial flow and axial flow propeller pumps. The flow dynamics and properties of centrifugal pumps are well established, G. F. Wislicenius reviewed the subject in *Mechanical Engineers Handbook* (1951) ed. L. S. Marks, McGraw Hill, N.Y., N.Y. Sealing of the shaft and bearings, between the drive mechanism and the propeller is of considerable importance in consideration of corpuscular damage.

DETAILED DESCRIPTION OF THE INVENTION

The following are the various volume and hemodynamic properties required for the adequate pumping of blood into the peripheral arterial tree: i. the actual volume of the chamber will depend on the size of the recipient, ii. stroke volumes ranging from 70 to 140 milliliters of blood depending on the recipient size, iii. systolic pressure of 140 mm Hg, iv. pulsatile blood flow and variable rate from 75 to 120 rpm which is adjustable based on physical activity.

In the normal heart the end diastolic volume is approximately 100 ml/m$^2$ body surface area. The ejection fraction varies from 50–55% to 80% in the normal human. The volume of the pump chamber of the present invention is large enough to satisfy the above criteria. The present invention is an implantable pump to assist or supplant one or more of the cardiac output functions. Subsequent descriptions will make it apparent that the same design also has applications for the movement of other fluids. Since blood is a colloidal solution composed of delicate cellular components, the design has incorporated features to minimize cellular damage, yet still maintain physiological blood pressures. A vaned conical rotor delivers reliable flow with minimal trauma to cellular constituents using currently implantable power sources. The pump that is proposed has one moving part and no valves within the pump itself, but rather in the conduit(s). Pressure is developed by altering the shape of the chamber without the use of a piston or a membrane that moves within the pump housing. In order to lessen cellular damage, blood flows along the outside of the rotor along the vanes, as opposed to through a whirling propeller. Due to the decreasing cross sectional area in moving from the base of a rotating cone to the apex, a net pressure and flow is established. The simplicity of the invention disclosed presently leads to improved durability and facilitates long term maintenance.

Figure 1:
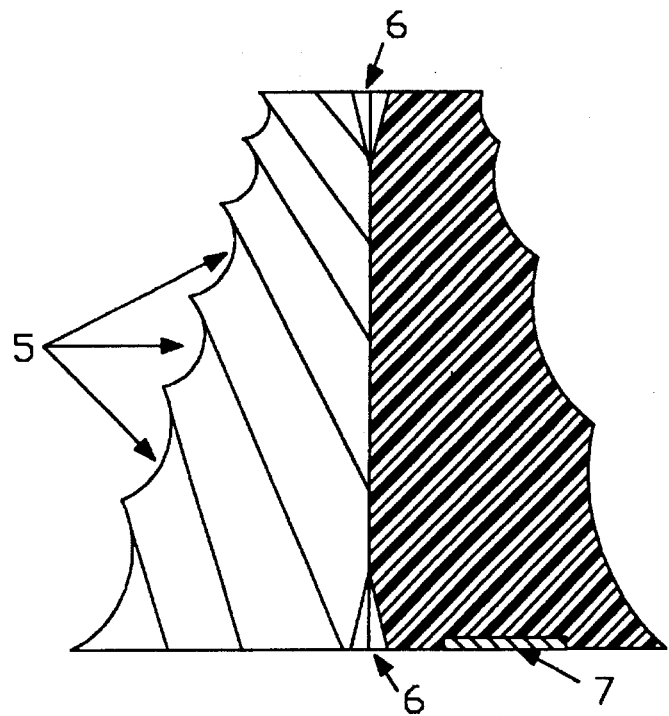
FIG. 1 is a partial cut-away view of the vaned rotor which resides within the pump housing and the electric drive motor assembly.
Figure 1:
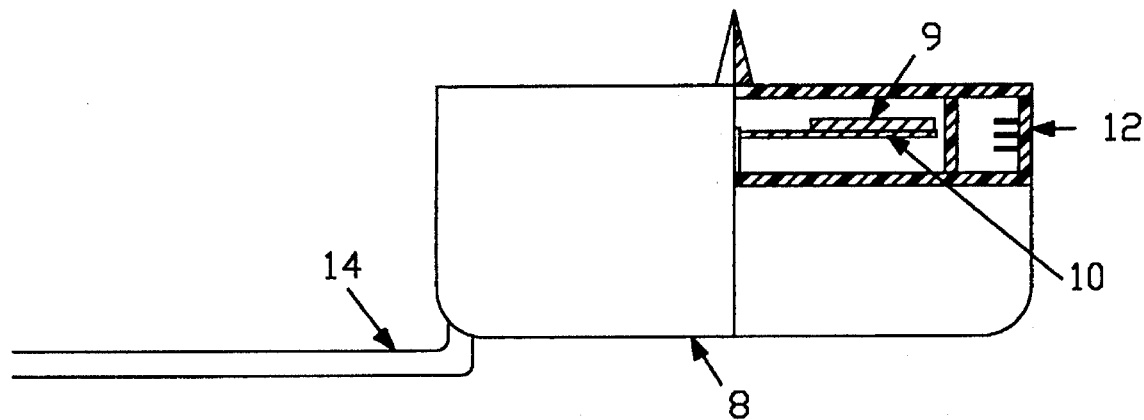

The conical rotor shown in FIG. 1 has several vanes, 5 which spiral up around the conical rotor body. Stroke volume and rotation speed are coordinated to provide a flow throughput of between 70 and 140 milliliters per second. In its preferred embodiment, the device will operate between 30 and 500 revolutions per minute (rpm), where size and device longevity are the constraining parameters. The rotor is molded from a polymeric material with a low shear modulus. A low shear modulus material is characterized by becoming pliable under the operating conditions of the device. A pliable rotor results in minimal trauma to the corpuscular elements of the blood. Useful rotor materials include, but are not limited to silastic, silicone rubbers and polyacrylates. As with other implantable materials, anticoagulation additives must be incorporated into the exposed polymeric surfaces. The inner lining of the rotor faces, 6 which seats to the axle pins is a near flawless single piece of a wear-resistant bearing material. The linings are molded seamlessly into the rotor to lessen plaque formation. The lining material is one of a number of biocompatible materials, such as titanium alloys or ceramics. A set of bar magnets, consisting of a least a single magnet are molded into the basal face of the rotor, 7 as a means of powering the rotor without direct connection to the motor.

A sealed electric motor, 8 screws onto the skirt at the base of the pump housing and is completely separated from the pump itself. At least one bar magnet, 9 is attached to a flywheel, 10 which is mounted to the electric motor shaft. In this way the motor is a sealed unit which is not exposed to the device recipients blood or tissue. The electric motor housing screws onto this skirt by means of interrupted threads, 12 similar to those in a breach plug. Several latches secure the motor housing, 13 to prevent separation from the pump housing. Since current nuclear batteries cannot provide sufficient power to drive the assist device for sustained periods, electrical leads, 14 are tunneled under the skin, outside of the body and then connected to an external battery 15 with a speed controller. Depending on the amount of physical activity to be performed, the rotation of the rotor can be increased from a resting speed comparable to the output of a healthy heart at 70 beats per minute to an active rate corresponding to 120 beats per minute with the use of the speed controller. The pacemaker leads of a design similar to those in current manufacture by the Intramedic and Medtronic Cos. are utilized for the electrical contacts to and from the speed controller and electrical motor.

The rotation of the electric motor propels the rotor at the same number of rpms through the interaction of the magnets. The rotor is not in physical contact with motor, but instead floats on the apical axle pin, 15 which is integral to the rotor housing and the basal axle pin, 16 which is mounted on the upper surface of the motor housing. In performance as a left ventricular assist device, blood is directed into the rotor invention by way of a sutured conduit from the apex of the deficient ventricle to the base of the rotor, 17. The rotation of the rotor pumps blood towards the rotor apex from which it is ejected by means of conduit, 18 similar to that serving as an inlet. The conduits are made of DACRON or a similar implantable material.

Figure 3:
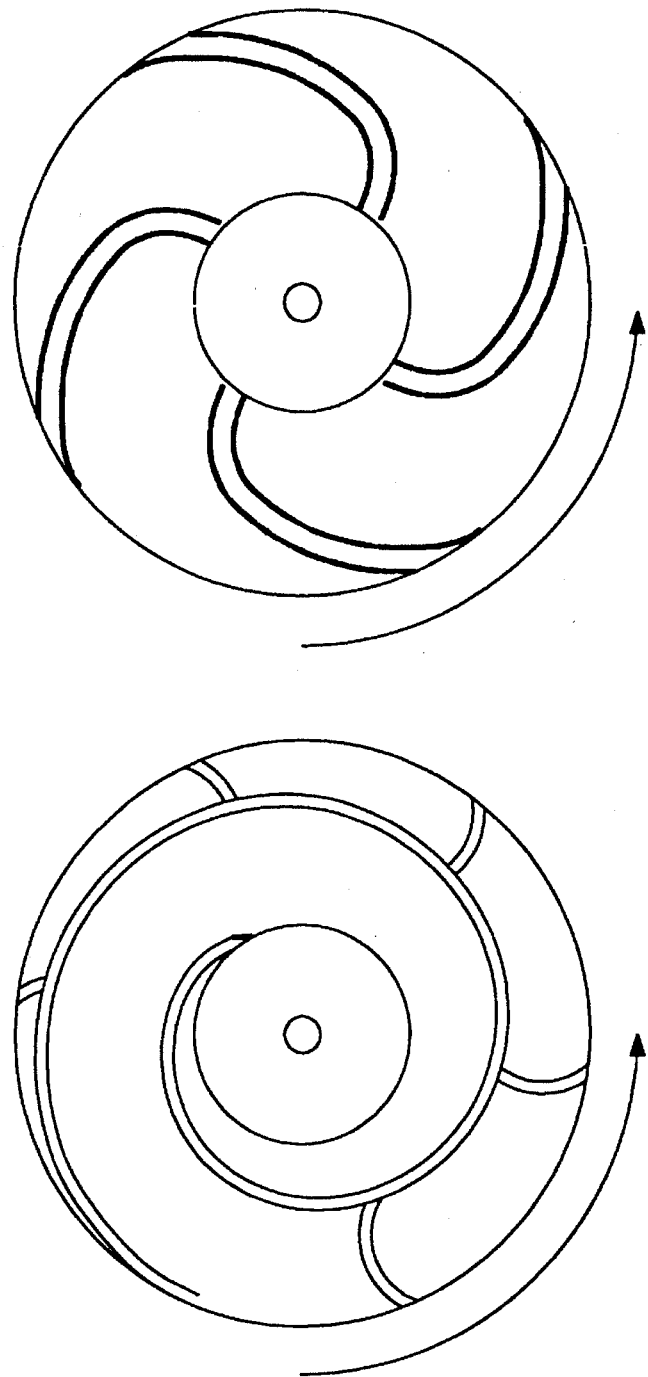
FIG. 3 is a transverse view of the base of the rotor showing two proposed designs for antistagnation contours for the rotor faces.
Figure 4:
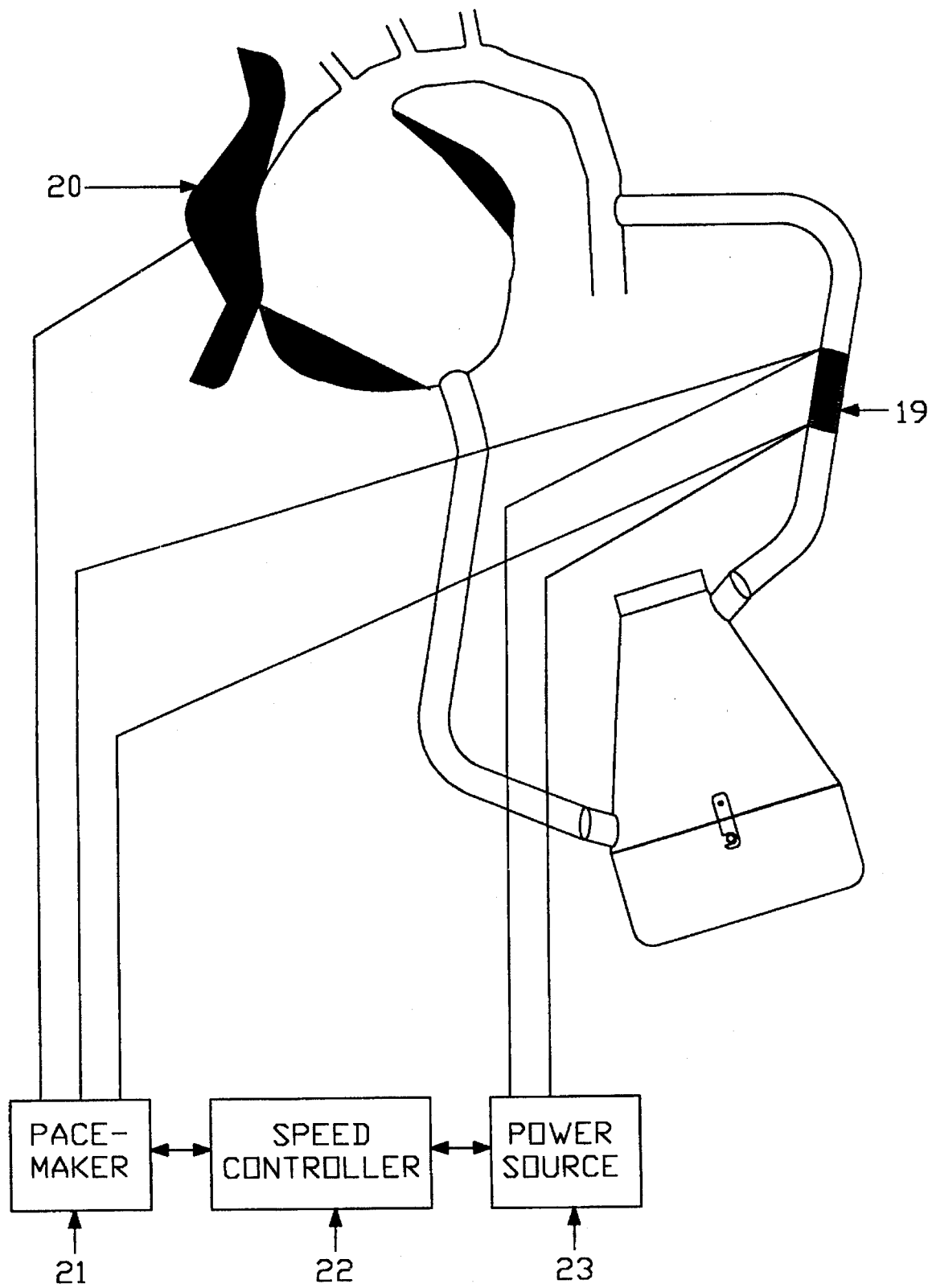
FIG. 4 is a schematic illustrating a spatial and control relationship between the ventricular assist device, the heart and the electrical components.

In order to minimize stagnation of blood at the rotor faces, spiral contours being grooves or ridges are incorporated to intersect with the rotor vanes 27, as shown in, FIG. 3. The continuation of these grooves into the opposing faces of the rotor from the vaned walls of the rotor serves to remove accumulated blood from the apical and basal surfaces, as well as the axle recesses.

For the pump to function as a left ventricular assist device the invention has an inlet portal at the broad base of the rotor housing and an outlet at or near the narrow apex of the rotor. Through the rotation of a rotor of the correct spiraled handedness for the direction of motor rotation, the blood is pressurized to left ventricle physiological blood pressures. In another embodiment, a rotor of opposite handedness for a given motor direction and a reversal of the inlet and discharge ports, compared to that described for left ventricular assist function allows the pump to serve to lessen the blood pressure. This function allows the pump to serve as a low pressure perfusion device for organs awaiting transplantation. This permits a more prolonged transit time with the maintenance of organ viability.

Pulsatile blood flow is obtained by use of a solenoid type flap valve, 19 which is installed within the conduit that connects the exit portion of the pump to the ascending aorta. The opening and closing of this flap valve is synchronous with the rotation of the rotor and the valve remains closed for a duration of time that is equal to the ejection time. This low profile flap valve is of the same design as those currently in use as prosthetic mitral and aortic valves. However, the invention utilizes a soft iron core molded into the valve so that as current flows through the solenoid coil, a magnetic field is established which closes the valve.

The back pressure resulting from this valve closure would be transmitted back through the pump and the conduit to the left ventricle which in turn acts as its own plenum. In situations where the left ventricle proves deficient, then a one-way flap or ball valve of the type regularly used in valve replacement surgery is placed in the conduit which leads from the left ventricle into the base of the rotor. The rotor itself is supported and spun about conical axles which are an integral part of the rotor housing. This type of axle design allows for maximal stability and minimizes vibration. These conical axles are composed of wear resistant material as are the rotor linings, so as to lessen friction and wear.

Pseudo-pulsatile blood flow may be produced by contouring the rotor differently with deeper and more tightly spiraled vanes on a portion of its surface, leaving the other portion of the rotor with shallower and more high pitched vanes. In such a manner, the pump stays primed, blood continues to be ejected and a differential pressure is established as the rotor completes a rotation.

Assuming that the conduction system of the heart is intact and functioning, an electrode is placed either in the coronary sinus or as a patch electrode sutured to the surface of the right atrium, 20. The electrodes are connected to a pacemaker, 21 that acts as a master synchronicity controller for the assist device speed controller, 22 and the power source, 23. When heart function dictates the use of solenoid flap valves, this control is also interfaced with the assist device and heart. The pacemaker wire is then tunneled under the skin together with the wires from the electric motor and connected into the external battery pack.

With a completely separate power source, if there is a failure of the electric motor, although surgical intervention would be required, a new motor is screwed back onto the base of the pump housing without having to interfere with the vascular connections from the left ventricle to the pump and from the pump to the aorta.

Figure 2:
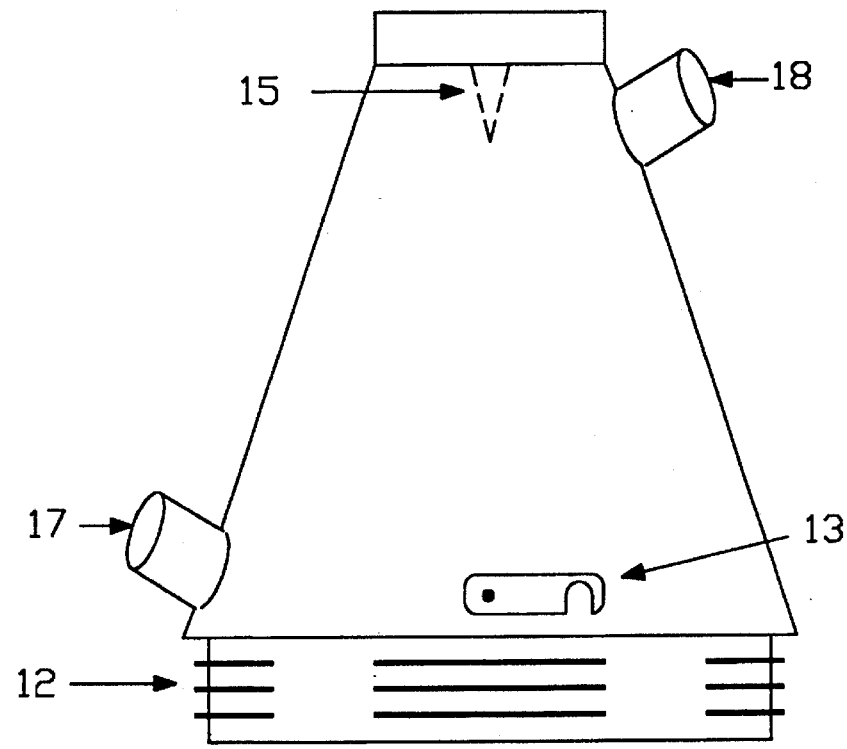
FIG. 2 shows the pump assembly indicating inlet and outlet ports and position of the electric motor.
Figure 2:
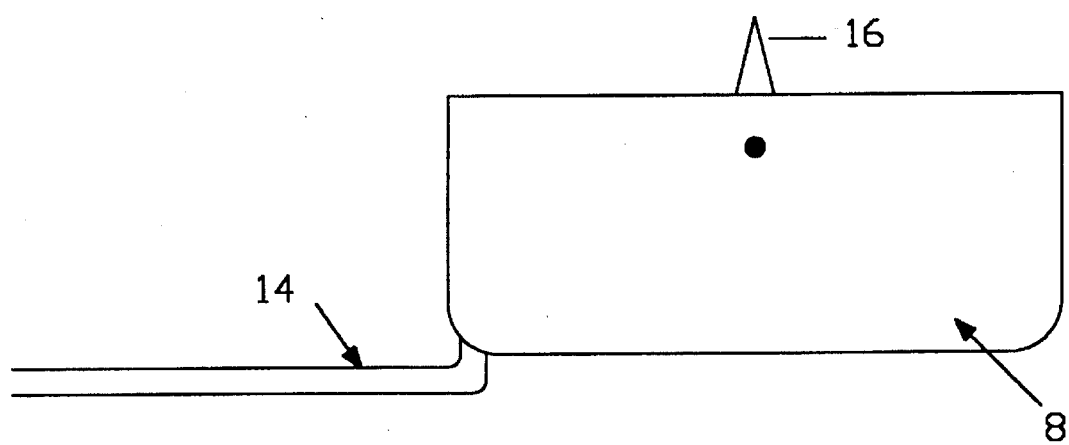

Since the top of the electric motor compartment, FIG. 2 constitutes the base of the pump housing, once the motor compartment is unscrewed the rotor is slid out from the pump body. In cases where rotor maintenance is required, vascular connections do not have to be interrupted.

In order to accommodate the pump within the thoracic cavity, the right middle lung lobe may be sacrificed since it contributes a minimal respiratory volume. Assuming that the recipient's pulmonary reserve is adequate, this can be accomplished without any significant respiratory embarrassment. Insertion of the pump in place of the middle lobe of the right lung allows for air flow through the remaining two lobes to cool the assist device.

It is to be understood that the ,forms of the invention shown herein are preferred examples and that modifications of the rotor design and arrangements may be accomplished within the spirit of the invention. The examples shown herein illustrate preferred embodiments, but are not intended to limit the scope of the adjoining claims.

The following innovations are claimed:

1. An implantable cardiac ventricular assist device comprised of:

(a) a conical rotor housing having a wall, possessing both interior and exterior surfaces, said rotor housing narrowing in diameter from a base to an apex, inlet and discharge portals which proceed from the exterior to the interior surfaces of said rotor housing, and an axle pin descending concentrically from the apex into the interior of said rotor housing;

(b) a conical rotor having an outside surface, a top and a bottom face, said rotor narrowing in diameter from the bottom to the top face, spiral vanes extending from the outside surface, having at least one bar magnet embedded in said conical rotor adjacent to the bottom face and a concentric indentation in the top and the bottom faces, said axle pin seating in the top face concentric indentation;

(c) a cylindrical electrical motor housing having a top exterior plane and an interior, with a second axle pin affixed concentrically to the top exterior plane, such that said second axle pin seats in the bottom concentric indentation of said conical rotor;

(d) an electric motor which is internal to said cylindrical electrical motor housing, having a drive shaft and a second multiplicity of bar magnets mounted so as to interact with said first bar magnet internal to said rotor; and (e) a means for forming a fluid tight closure between said cylindrical electric motor housing and said conical rotor housing.

2. The ventricular assist device as set forth in claim 1, wherein the indentations of said rotor are lined with a wear resistant, biocompatible material.

3. The ventricular assist device as set forth in claim 2, wherein said inlet portal is located on the rotor housing wall, adjacent to the base and said discharge portal is opposed to said inlet portal on the rotor housing wall, adjacent to the apex.

4. A ventricular assist device as described in claim 1, further including an electronic power source and synchronous controller therefor, having:

(a) electrical leads to said electric motor;

(b) a solenoid flap valve located adjacent to said discharge portal;

(c) a second set of electrical leads to said solenoid flap valve;

(d) a power source; and (e) an electronic means for the synchronous adjustment of said electric motor rotation rate and said solenoid flap valve cycle rate by connection to said electric leads, said second set of electrical leads and said power source.

5. The electronic power source and synchronous controller of claim 4 further comprising:

(f) a pacemaker; and (g) a multiplicity of pacemaker leads that interconnect said pacemaker, with said speed controller, said power source and said solenoid flap valve.

6. The ventricular assist device as set forth in claim 4, wherein said rotor has at least one antistagnation groove on each of the top and bottom faces.

7. The ventricular assist device as set forth in claim 6, wherein said rotor vanes are asymmetric in pitch and depth relative to a rotation axis defined by said axle pins.

8. The controller as set forth in claim 4 wherein the device capable of synchronous adjustment of the electric motor rotation rate and flap valve cycle rate is a speed controller.

* * * * *